United States Patent [19]

Hancock et al.

[11] Patent Number: 4,816,395

[45] Date of Patent: Mar. 28, 1989

[54] METHOD FOR PREDICTING CHEMOSENSITIVITY OF ANTI-CANCER DRUGS

[75] Inventors: Miriam E. C. Hancock; Helene S. Smith, both of Oakland; Adeline J. Hackett, Orinda, all of Calif.

[73] Assignee: Peralta Cancer Research Institute, Oakland, Calif.

[21] Appl. No.: 811,552

[22] Filed: Dec. 19, 1985

[51] Int. Cl.$^4$ ............................................... C12Q 1/02
[52] U.S. Cl. ..................................... 435/29; 436/800; 436/813
[58] Field of Search ............................................ 435/29

[56] References Cited

U.S. PATENT DOCUMENTS

| 4,559,299 | 12/1985 | Rotman | 435/240.242 |
| 4,689,311 | 8/1987 | Weltman | 435/29 |
| 4,734,372 | 3/1988 | Rotman | |

OTHER PUBLICATIONS

Rotman—Chem. Abst. vol. 104 (1986), pp. 180,198t.
Kaufman et al. (1978) J. Biol. Chem. 257:5852–5860.
Rosowsky et al. (1982) J. Biol. Chem. 257:14162–14167.
Johnston et al. (1983) Proc. Natl. Acad. Sci. U.S.A. 80:3711–3715.

*Primary Examiner*—Sam Rosen
*Attorney, Agent, or Firm*—Townsend and Townsend

[57] ABSTRACT

As assay for determining the sensitivity of an individual patient tumor to particular chemotherapeutic drugs relies on growth of the neoplastic tumor cells in a mass culture. The mass culture medium provides metabolites essential for the growth of the cells, even in the presence of the particular drug being tested, which is usually an anti-metabolic drug. The mass culture of cells is exposed to a labelled analog of the drug, and the uptake of the labelled drug analog determined. By comparing the amount of the drug uptake by the neoplastic cells with that of the corresponding normal cells, drug sensitivity may be assessed. The method is particularly useful with fluorescently-labelled drugs where the uptake may be assessed by use of a fluorescence activated cell sorter.

18 Claims, 1 Drawing Sheet

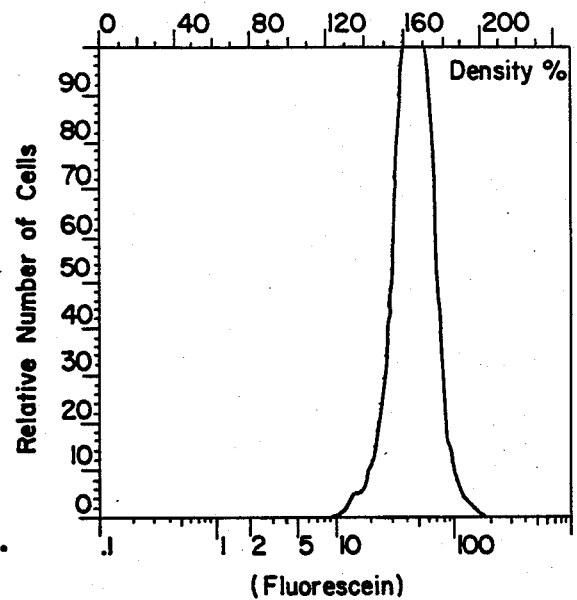
FIG._IA.
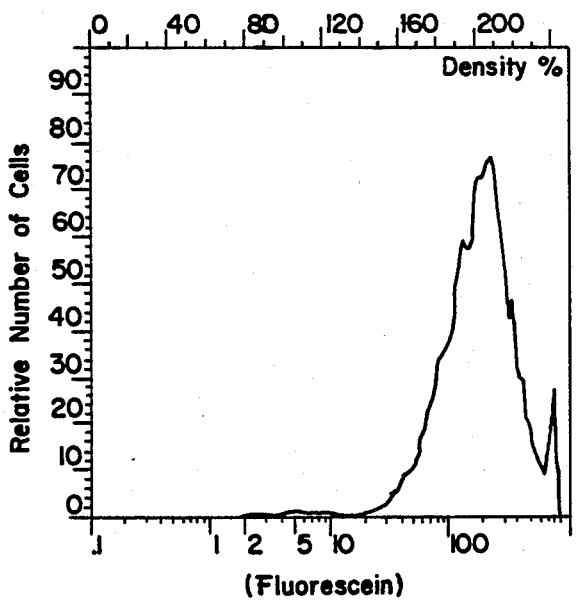
FIG._IB.

METHOD FOR PREDICTING CHEMOSENSITIVITY OF ANTI-CANCER DRUGS

BACKGROUND OF THE INVENTION

1. Field of the Invention

The present invention relates generally to assays for predicting chemosensitivity, and more particularly, to a method capable of predicting the sensitivity of neoplastic cells to particular anti-cancer drugs.

Chemosensitivity of a patient tumor to particular anti-cancer drugs has heretofore been assessed in clonogenic assays, typically in agar. Cells are divided from a biopsy specimen, and single cells grown in the assay culture. Proliferating cultures are then exposed to the drug, and chemosensitivity assessed based on observed toxicity. While such assays are successful for many types of tumors, they are much less successful for certain tumors, such as breast tumors, where the cells are not easily cloned. Moreover, the effectiveness of such assays is greatly reduced if the culture medium contains components which affect the toxicity of the drug being tested.

Therefore, it would be desirable to provide alternative chemosensitivity assays which do not require cloning of the tumor cells and which do not rely on the direct observation of toxicity. It would be particularly desirable to provide such assays which are highly accurate, convenient to perform, and relatively inexpensive.

2. Description of the Relevant Art

Kaufman et al. (1978) J. Biol. Chem. 257:5852–5860, describe the use of a fluorescence activated cell sorter to quantitate levels of dihydrofolate reductase (dhfr) levels in methotrexate-resistant cell lines. Rosowsky et al. (1982) J. Biol. Chem. 257:14162–14167 describe the preparation of a particular fluorescent methotrexate analog. Johnston et al. (1983) Proc. Natl. Acad. Sci. USA 80:3711–3715, describe the use of classical fluctuation analysis to demonstrate dhfr gene amplification upon exposure to methotrexate. Cells with the highest levels of dhfr were selected by exposure to fluoresceinated methotrexate and sorting using a FACS.

SUMMARY OF THE INVENTION

The present invention provides for the non-toxic assay of toxic chemotherapy drugs in mass culture of neoplastic cells from an individual patient. The assay is useful for predicting the therapeutic value of a particular drug for the individual patient being tested. Clumps of non-dissociated tumor cells are grown in mass culture in a predefined medium and, after proliferative growth is achieved, exposed to the chemotherapeutic drug of interest, which drug has been labelled or is naturally detectable. e.g., fluorescent. The medium is capable of supporting growth of the culture even in the presence of the toxic drug. That is, the medium includes components which are able to provide the necessary metabolites, the production of which may be blocked by the chemotherapeutic drug. Sensitivity or susceptibility of the tumor cells to the drug is then assessed by observing the uptake of the drug in the cultured tumor cells. It has been found by the inventors herein that an abnormal uptake of the drug, either increased or decreased, relative to the uptake in a normal cell culture, correlates with tumor cells which are not susceptible to treatment with that drug. In contrast, uptake of the labelled drug in an amount which corresponds to that of normal cells indicates that the tumor cells should be sensitive to treatment with that drug.

In the exemplary assay, neoplastic breast epithelial cells are cultured in a predefined medium which will support their growth in the presence of methotrexate. Once viable growth is achieved, the cells are exposed to fluoresceinated methotrexate, and the fluorescently labelled cells separated using a fluorescence activated cell sorter. The cells in a particular phase of the growth cycle are first sorted based on their DNA content. Cells in a single phase are then analyzed for their content of fluoresceinated methotrexate, and the amount of the label (which corresponds to the uptake of the drug) compared with a representative value for normal (non-neoplastic) breast epithelial cells. An increased uptake of the fluoresceinated methotrexate in the neoplastic cells relative to the normal cells is indicative that the neoplastic cells are likely to be resistant to methotrexate therapy.

BRIEF DESCRIPTION OF THE DRAWINGS

FIG. 1 is a comparison of the uptake of fluoresceinated methotrexate in normal cells (FIG. 1A) and neoplastic cells (FIG. 1B). The scales on the graphs are arbitrary, but the same for each of the two graphs. The fluorescein content of the neoplastic cells is substantially higher than that of the normal cells.

DESCRIPTION OF THE SPECIFIC EMBODIMENTS

The present invention is a rapid and highly sensitive assay for predicting the sensitivity of neoplastic cells from an individual cancer patient to a particular chemotherapeutic drug. Neoplastic cells are grown in mass culture under conditions where sensitive and resistant cells are indistinguishable. The cells are then exposed to the drug, and the uptake of the drug in the cultured cells observed. The amount of drug uptake, which is assessed based on a natural characteristic of the drug (e.g., fluorescence) or a label conjugated to the drug, is then compared with the amount of drug uptake in a culture of normal cells of the same type. Tumor cells which are sensitive to the drug will normally display substantially the same drug uptake as that for normal cells, while resistant tumor cells will display an abnormal drug uptake, either greater than or less than the drug uptake in normal cells.

The assay methods of the present invention are useful with a wide variety of neoplastic cells, including both solid tumor cells and hematopoietic neoplasms. Exemplary solid tumors include breast tumors, liver tumors, kidney tumors, colorectal tumors, and the like. The tumor cells may be of epithelial origin (carcinomas), arise in the connective tissue (sarcomas), or arise from specialized cells such as melanocytes (melanomas) and lymphoid cells (lymphomas), and the like. Moreover, the neoplastic cells may be derived from either primary tumors or metastatic tumors. In the exemplary embodiment, the chemosensitivity of both primary and metastatic breast carcinomas is investigated.

The anti-neoplastic drugs which may be assessed by the assay of the present invention include naturally fluorescent drugs, such as adriamycin, and drugs capable of being conjugated to a detectable label, where altered drug uptake in neoplastic cells (compared to normal cells) is a function of drug resistance. Of particular interest are anti-metabolic drugs, i.e., the drugs which interfere with or block a metabolic pathway responsible for the production of an essential metabolite within the cell. Typically, the drug will interfere with at least one enzyme in the metabolic pathway. Illustrative of the anti-metabolic drugs are methotrexate (amethopterin); 5-fluorouracil; 6-mercaptopurine; 6-thioguanine; cytosine arabinoside; 5-azacytidine; and hydroxyurea. The invention is exemplified with methotrexate which blocks dihydrofolate reductase (dhfr) which catalyzes the reduction of dihydrofolic acid to tetrahydrofolic acid.

Drugs which are not naturally fluorescent must be bound to a detectable label to allow quantitation of the uptake of the drug, as will be described in detail hereinafter. A variety of labels will be useful, including fluorescent labels, such as fluoroscein merocyanine, rhodamine, and the like; radionuclides, such as $^3H$, $^{125}I$, $^{32}P$, $^{14}C$, $^{36}Cl$, $^{35}S$, and the like; luminescent labels, such as bacterial and firefly luciferase; and enzyme labels, such as horseradish peroxidase, glucose oxidase, $\beta$-galactosidase, and the like.

Particularly useful are fluorescent labels which allow for convenient sorting and quantitation in commercially-available fluorescence-activated cell sorters, such as those manufactured by Becton-Dickinson, Sunnyvale, Calif. Methods for conjugating fluorescent labels, such as fluorescein, to particular chemotherapeutic drugs are known in the art. For example, a method for conjugating fluorescein to methotrexate is taught by Gapski et al. (1975) J. Med. Chem. 18:526–528. An alternative method for producing a fluorescent methotrexate derivative is taught by Rosowski et al. (1982), supra.

To perform the assays of the present invention, it is first necessary to grow out a mass culture of the neoplastic cells. In the case of a solid tumor, the source of the neoplastic cells will typically be a biopsy specimen. The biopsy specimen is disected into small clumps, digested with proteinases and the clumps plated in a flask containing an appropriate growth medium. The neoplastic cells proliferate and migrate from the clump to form a monolayer in the flask. After the monolayer reaches confluence, cells are harvested from the monolayer and replated at subconfluence. The cells are then allowed to grow until they are rapidly dividing. A method suitable for culturing both normal and neoplastic epithelial cells is described in U.S. Pat. No. 4,423,145, the contents of which are incorporated herein by reference.

When the cells are rapidly dividing (which may be assessed by observing the mitotic configuration), they are exposed to the drug at a concentration depending on the particular drug, usually in the range from about 1 to 100 $\mu$M, more usually from about 10 to 50 $\mu$M. The particular concentration is chosen to result in a nontoxic, saturated intracellular level of the drug. After incubation with the drug for a preselected period, typically from about 1 to 48 hours, more typically about 24 hours, the cells are sorted into G1 and G2 fractions on the basis of DNA content. To do so, the cells are stained with a vital DNA stain, typically a fluorescent stain, and sorted using a FACS. Either the G1 or the G2 fraction, or both, may be used for further analysis.

Further analysis consists of quantifying the amount of drug taken up by individual cells. The use of a fluorescent label (either natural or conjugated) and the FACS is ideal for such a quantitation step, since the FACS is capable of quantitating the label in individual cells. Other methods, however, for quantitating the labels will also find use. Fluorescent analyzers will be able to measure the total fluorescence given off by a known quantity of cells. The amount of label per cell may then be calculated based on the known number of cells.

The present invention relies on comparing the amount of drug taken up by the neoplastic cells with the amount of drug taken up by corresponding cells. The corresponding normal cells are cells of the same cellular type as the neoplastic cells. For example, the drug uptake in neoplastic mammary epithelial cells will be compared with the drug uptake in normal mammary epithelial cells.

The variation between drug uptake in normal cells and that in neoplastic cells will be substantially the same when the neoplastic cells are susceptible to the drug being tested. When the neoplastic cells are not sensitive to the particular drug, the drug uptake in the neoplastic cells will vary, being either greater than or less than the drug uptake in the normal cells. The amount of variability will be at least $\pm 25\%$, usually being at least $\pm 50\%$, often being as much as $\pm 100\%$ and sometimes being as large as $\pm 500\%$, or larger. In the case of mammary epithelial cells treated with labelled methotrexate, the neoplastic cells which are not sensitive to the methotrexate will normally display a drug uptake which is at least 50% higher than that of normal mammary epithelial cells, usually being 300% higher, or more.

The results of the assay are useful for determining the value of using a particular drug for treatment of the patient's tumor. The sensitivity of the tumor cells to the drug, however, may change if the tumor regresses and then recurs, and it will be advisable to retest the patient at such time to determine any variation in drug sensitivity.

The following examples are offered by way of illustration, not by way of limitation.

EXPERIMENTAL

Fluorescent labelled methotrexate (F-Mtx) was prepared by the method of Gapski et al. (1975) supra., as modified by Wahl et al. (unpublished). Fluorescein isothiocyanate (750 mg) was reacted with 1,5-diaminopentane (2 g) in 10 ml dimethylsulfoxide for 4 hours at room temperature. The product was applied to a DEAE-cellulose column and eluted with 0.3M NH$_4$HCO$_3$ pH 7.8. The resulting thiourea was lyophilized, brought into solution with 0.1N NH$_4$OH, and precipitated using 1N HCl. The resulting solid fluorescein-diaminopentane (109 mg) was then mixed with 100 mg methotrexate, 200 mg 1-ethyl-3(3-dimethylaminopropyl) carbodiimide, and 12 ml dimethylformamide. The mixture was stirred well and incubated in the dark for 20 minutes at room temperature. Ether (120 ml) was added next, and the mixture was spun at 3000 rpm for 15 minutes. After decanting the supernate, the remaining pellet was airdried. The pellet was then dissolved in 50 ml 0.1M NH$_4$OH, stirred, and filtered through a 0.45 $\mu$m nitrocellulose filter. The filtrate was neutralized to pH 6.8–7.0 with 5M HCl and refiltered. The filter plus precipitate was then lyophilized and dissolved in 25 ml 50 mM NH$_4$OH. Next, the solution was loaded onto a 15 ml column of DEAE-trisacryl which had been washed extensively with water. The loaded column was then washed overnight with 1 liter of 0.1M NH$_4$HCO$_3$ in 20% acetonitrile, then washed with 30 ml 0.25M NH$_4$HCO$_3$ in 20% acetonitrile. Fractions were collected and examined for fluoresceinated product (F-Mtx) by thin layer chromatography using a Polygram cell 300 PE1/UV254 (Sybron Brinkmann). The solvent was 0.25M $NH_4HCO_3$ in 20% acetonitrile which separates unreacted fluorescein-diaminopentane and methotrexate from fluoresceinated methotrexate. The positive fractions were pooled again and neutralized with 5M HCl. Filtration, lyophilization and redissolution in 25 ml 50mM $NH_4OH$ were repeated as described above. Finally, the F-Mtx was lyophilized and resuspended in 0.01M $NH_4OH$ to a final concentration of 1 mM. This procedure yielded highly pure and stable F-Mtx when stored in solution at −20° C.

Cultures of non-malignant and malignant human mammary epithelial cells were prepared from biopsy and mastectomy specimens taken from a number of individuals as described by Stampfer et al. (1980) In Vitro 16:415–425.

Briefly, tumor tissue was dissected away from fat and stroma and then finely minced. The tissue was transferred to a 50 ml conical centrifuge tube containing medium with 10% FCS, 5 ug/ml insulin, antibiotics, plus 150 U/ml collagenase and 100 U/ml hyaluronidase. Enzymatic digestion proceeded at 37° C. with gentle agitation by placement of the centrifuge tubes on a tube rotator. The collagenase acts to break down the surrounding stromal tissue, while the hyaluronidase digests the basement membrane surrounding the mammary epithelial ducts and lobules.

After overnight incubation, the suspension was pelleted at 600 g for 10 minutes, and the pellet was resuspended in fresh enzyme digestion mixture in 15 ml or 50 ml plastic centrifuge tubes. The tubes were replaced on the tube rotator at 37° C., and at intervals, the suspension was observed under the light microscope. The reaction was stopped when clumps of cells (organoids) were observed free from attached stromal elements. At this point, the suspension was placed on 150, 95, or 51 µm pore sized polyester filters (pecap monofilament polyester screen, Tetko, Inc., Monterey Park, CA) and the filters washed with warm medium. The filters were then inverted and the organoids were washed off into a centrifuge tube. The collected organoids and the filtrates were pelleted at 600 g for ten minutes, and then resuspended into cell growth medium or preservation medium for storage.

The growth medium consisted of 30% Ham's F12, 30% DMEM, 39.5% conditioned medium from 3 human cell lines, 0.5% fetal calf serum 10 ug/ml hydrocortisone, 5 ng/ml epidermal growth factor, $10^{-8}M$ triiodothyronine, $10^{-9}M$ estradiol, and 1 ng/ml cholera toxin, as described previously (Stampfer et al., In Vitro, 16:415–425, 1980).

Either fresh or previously frozen multicellular organoids were plated into a tissue culture flask, allowed to attach, fed with growth medium, and incubated at 37° C. in a humidified atmosphere with 5% $CO_2$. The cells migrated and proliferated. After 4–6 days, cells were harvested for experimentation.

To determine the intensity of staining with F-Mtx, approximately $10^6$ cells from proliferating primary or secondary cultures of non-malignant and malignant human mammary epithelial cells were grown in rapidly dividing subconfluent layers, as described above, and incubated with 35 µM F-Mtx in medium for 24 hours at 37° C. This concentration of F-Mtx resulted in saturating intracellular levels and was nontoxic.

The cells were next sorted into $G_1$ and $G_2$ fractions on the basis of DNA content. To do this, the cells were trypsinized, stained with a vital DNA stain, Hoechst #33342 (10 µM), at 37° C. for 45 minutes with frequent gentle agitation, and sorted using a modified Becton Dickenson fluorescence activated cell sorter (FACS II) based on the wavelength of the DNA stain (360 nm) to produce at least $2 \times 10^4$ $G_1$ or $G_2$ cells in 0.1 ml medium. The $G_1$ and $G_2$ populations were then reanalyzed for uptake of F-Mtx using the FACS II based on the wavelength of fluoroscein (488 nm).

Histograms typical of F-Mtx content in short-term cultures of a normal mammary epithelium (normal reduction mamoplasty specimen 437E) and a metastatic tumor cell (pleural effusion specimen 523KH) are shown in FIGS. 1A and 1B, respectively. The $G_2$ fluorescence peak of the normal cell (FIG. 1A) was at 40 arbitrary units with a relatively narrow coefficient of variation of 0.064. The metastic specimen, in contrast (FIG. 1B), had a $G_2$ fluorescence peak at 110 arbitrary units with a broader coefficient of variation of 0.11. In general, the normal specimens demonstrated narrow distributions of F-Mtx staining both in $G_1$ and $G_2$, while the metastatic cells showed much greater variation.

In order to assess the efficacy of this assay for predictive chemotherapy testing, F-Mtx uptake in short-term cultures of non-malignant and malignant breast cells was compared with the donors' clinical histories. The results are set forth in Table 1. Cultured cells from the normal specimen 437E (FIG. 1A) were run in all experiments as a control, and normalized fluorescence values based on the control fluorescence value are reported in Table 1. All of the fluorescence values for the non-malignant cultures were strikingly similar to the control value. The average normalized F-Mtx staining intensity of the 15 non-malignant specimens were 1.0±0.062. Included among these were cultured non-malignant mammary epithelium, cultured pleural effusions containing no tumor cells, and cultured fibroblasts from skin and breast.

Six primary carcinomas from patients having received no previous therapy were also examined. Four of these specimens showed F-Mtx staining intensities approximately equal to the control value (although there was perhaps slightly more variation) while the fifth and sixth specimens (648T and 763T) differed from the non-malignant cells by more than five standard deviations (a significant level of $p < 0.00001$).

Of the eight metastatic specimens tested, seven showed elevated F-Mtx staining patterns ranging from 1.5–8.1. All of these patients had either relapsed on methotrexate or were initially not responsive to therapies containing methotrexate. In contrast, the eighth specimen (576PE) showed a normal level of F-Mtx uptake. Patient 576PE, however, had not relapsed on methotrexate therapy, and the patient's only contact with the drug had been in a combination adjuvant protocol that was completed 11 months prior to relapse.

TABLE 1

| Specimen | Patient Age | Tissue Pathology Prior to Culture | DNA Content | Relative F-Mtx Staining Intensity[1] | Relevant Clinical History |
|---|---|---|---|---|---|
| NON-MALIGNANT | | | | | |

TABLE 1-continued

| Specimen | Patient Age | Tissue Pathology Prior to Culture | DNA Content | Relative F-Mtx Staining Intensity[1] | Relevant Clinical History |
|---|---|---|---|---|---|
| | | Non-malignant Mammary Epithelium | | | |
| 161E | 17 | Intralobular fibrosis | 2.1 | 1.0 | No therapy |
| 337E | 59 | Focal duct ectasia | 2.0 | 1.1 | No therapy |
| 356E | 21 | Normal reduction | 2.0 | 1.0 | No therapy |
| 399E | 20 | Normal reduction | 2.0 | 1.0 | No therapy |
| 437E | 17 | 10% Normal, 90% Fibrosis | 2.0 | 1.0 | No therapy |
| 483HRA | 29 | 80% Normal, 20% Fibroadenosis | ND[3] | 1.0 | No therapy |
| 527EB (A) | NA[2] | 80% Normal, 20% Fibrosis | ND | 1.0 | No therapy |
| 419P | 90 | 90% Normal, 10% intraductal hyperplasia | 2.0 | 1.0 | No therapy |
| 433P | 67 | 60% Normal. Intraductal hyperplasia, Micro-fibro-adenomatosis | 2.0 | 0.8, 1.1 | No therapy |
| 469P | 28 | 20% Normal, 80% adenosis | 2.0 | 1.0 | No therapy |
| 571P | 37 | 90% Normal, 10% adenosis | 2.1 | 1.0 | No therapy |
| | | Pleural Effusions Containing No Tumor | | | |
| 567PE | 84 | 95% Lymphocytes, 3% mesothelium, 1% histiocytes, 1% neutrophils | 2.0 | 1.0 | Prior Therapy was T[2] |
| 580PE | 57 | 55% histiocytes, 20% neutrophils, 15% lymphocytes, 10% mesothelium | 2.1 | 1.0 | Same patient as 582LiM |
| | | Normal Fibroblasts | | | |
| 515F | 43 | Normal skin fibroblast | 2.0 | 1.0 | Same patient as 513AM & 600PE |
| 519F | 48 | Normal skin fibroblast | 2.0 | 1.0 | Same patient as 521AM |
| | | CARCINOMA CULTURES | | | |
| | | Primary Carcinomas | | | |
| 192T | 42 | Infiltrating lobular | 2.0 | 0.8 | No prior therapy. |
| 335T | 58 | Infiltrating lobular | ND | 0.8, 0.9 | No prior therapy. |
| 407T | 43 | Invasive ductal | 2.0 | 1.0 | No prior therapy. |
| 469T | 28 | Infiltrating ductal | 2.0 | 0.9 | No prior therapy. |
| 648T | 42 | Infiltrating ductal Marked nuclear anaplasia | 2.0 | 1.4 | No prior therapy. |
| 763T | 37 | N.D.[3] | 2.2 | 2.9 | One month after beginning C,M,F[2]. |
| | | Metastases | | | |
| 468AM | 34 | Pertioneal effusion | 4.4 | 4.2 | Immediately after relapse in M,F,T[2]. |
| 513AM | 45 | Peritoneal effusion | 2.0 | 4.3 | No prior therapy. Failed C,M,F[2] treatment beginning 2 weeks after this specimen. Same patient as 515F, 523PE, 600PE. |
| 521AM | 48 | 95% malignant peritoneal effusion, 5% lymphocytes | 2.9 | 8.1 | 1 month after relapse on M,F[2]. |
| 523PE | 45 | Pleural effusion | (2.0) | 5.0 | No response to C,M,F[2]. |
| 576PE | 56 | NA[3] | 2.4 | 1.1 | 11 months after adjuvant C,M,F,A[2]. |
| 582LiM | 57 | Liver matastasis, infiltrating ductal carcinoma | 1.6 | 3.0 | 2 months after failing C,M,F,A[2] therapy. |
| 600PE | 45 | Pleural effusion | 2.0 | (1.5) broad subpopulation | 5 months after failing C,M,F[2] therapy. |
| 764PE | 37 | Pleural effusion | 3.3 | 3.7 | 1 month after beginning C,M,F therapy; same patient as 763T. |

[1] Normalized value obtained by dividing sample fluorescence value by fluorescence value of sample 437E. Thus, the relative staining intensity of sample 437E is 1.0.
[2] Abbreviations: M = Methotrexate; F = Fluorouracil; C = Cytoxan; A = Adriamycin; T = Tamoxifen.
[3] NA: Not available; ND: Not done.

Table 1 also summarizes the DNA content of various specimens. As expected, all of the non-malignant specimens contained a diploid amount of DNA. Those cells cultured from primary carcinomas were also diploid. In contrast, most of the specimens derived from metastases were aneuploid, clearly identifying them as malignant cells. The DNA contents were unrelated to F-Mtx uptake since cultures with diploid DNA contents (648T, 513AM, 523AM) showed increased F-Mtx uptake, while specimen 576PE had normal F-Mtx uptake despite an aneuploid DNA content.

Several specimens shown in Table 1 were derived from a single patient over a period of six months (Table 2). Specimen 513AM was of particular interest since the donor had received no treatment at the time her ascites was tapped. The cells taken from a peritoneal effusion showed a 4.3-fold increase in uptake of F-Mtx over both the standard control and her own normal fibroblasts (515F). This patient showed no response to subsequent therapy containing methotrexate. The presence of resistant cells in a tumor population before exposure to any form of therapy clearly demonstrates the value of predictive testing prior to treatment, and could be exceedingly useful information for the clinician designing therapeutic regimens.

TABLE 2

Analysis of Multiple Specimens From a Single Patient with Metastatic Breast Cancer

| Specimen | Date | Clinical History | Relative F-Mtx Staining Intensity[1] |
|---|---|---|---|
|  | March | Mastectomy for primary Cancer |  |
| 513AM | 11/17 | Tumor - peritoneal effusion | 4.3 |
| 515F | 11/22 | Fibroblasts cultured from skin metastasis | 1.0 |
|  | 11/29 | Began C,M,F[2] therapy |  |
| 523PE | 12/02 | Tumor-pleural effusion |  |
|  | 01/04 | C,M,F[2] terminated, progressive disease | 5.0 |
|  | 01/30–03/12 | Radiation therapy |  |
|  | 05/03 | Therapy with A[2] |  |
| 600PE | 05/23 | Tumor-pleural effusion | 1.5 (very broad subpopulation |

[1]Relative to both the 437E control and the patient's own fibroblasts.
[2]Abbreviations: C = Cytoxan; M = Methotrexate; F = 5-fluorouracil; A = Adriamycin.

Another specimen (523PE) which was taken two weeks after commencing low dose methotrexate thereapy was similar to 513AM and showed increased uptake of F-Mtx. A third speciment (600PE) which was removed four months after terminating methotrexate thereapy and following additional radiation thereapy, was clearly different. This specimen contained only a small subpopulation demonstrating increase uptake of F-Mtx, with the majority of cells having more normal uptake of F-Mtx. Other properties of the 600PE cells also differed from the first two lesions including morphology and increased capacity to proliferate and generate cell lines. These observations illustrate that the generation of tumor heterogeneity is a function of malignant progression by demonstrating how a population with increased growth potential and more normal F-Mtx uptake can overgrow and dominate a metastatic tumor. The results further illustrate how patients who initially fail a given drug regimen might subsequently become more responsive to the same drug.

Although the foregoing invention has been described in some detail by way of illustration and example for purposes of clarity of understanding, it will be obvious that certain changes and modifications may be practiced within the scope of the appended claims.

What is claimed is:

1. An assay for determining drug sensitivity of a neoplasm, said assay comprising:
    culturing cells from the neoplasm in a mass culture;
    exposing the mass culture to the drug, wherein the drug is naturally fluorescent or bound to a detectable label;
    measuring the amount of drug which is incorporated in the cells of the culture as a result of such exposure based on the amount of fluorescence or label in the cells; and
    comparing the measured amount of label incorporated in the cultured neoplastic cells with a representative amount of drug incorporated in cultured normal cells.

2. An assay as in claim 1, wherein the cultured cells are synchronized into the same cell cycle phase prior to exposure to the drug.

3. An assay as in claim 1, wherein the label is a fluorescent label.

4. An assay as in claim 3, wherein the label is measured in a fluorescence activated cell sorter.

5. An assay as in claim 3, wherein the label is measured in a fluorescence analyzer.

6. An assay as in claim 1, wherein the neoplasm is a solid tumor.

7. An assay as in claim 6, wherein the solid tumor is selected from the group consisting of breast tumors, lung tumors, colorectal tumors, and liver tumors.

8. An assay as in claim 7, wherein the solid tumor is a breast tumor.

9. An assay as in claim 1, wherein the neoplasm is a hematopoietic neoplasm.

10. An assay as in claim 1, wherein the drug is an anti-metabolite.

11. An assay as in claim 10, wherein the anti-metabolite drug is selected from the group consisting of methotrexate, 5-fluorouracil, 6-mercaptopurine, 6-thioguanine, cytosine arabinoside, 5-azacytadine, and hydroxyurea.

12. An assay for determining methotrexate sensitivity of a mammary epithelial tumor, said assay comprising:
    culturing cells from a sample of the tumor in a mass culture;
    exposing the cells in the mass culture to fluorescently-labelled methotrexate;
    measuring the amount of fluorescent label incorporated in the cultured cells with a representative amount of fluorescently-labelled methotrexate incorporated in cultured normal mammary epithelial cells.

13. An assay as in claim 12, wherein the cells are synchronized into the same cell cycle phase prior to exposure to the fluorescently-labelled methotrexate.

14. An assay as in claim 13, wherein the tumor cells in the mass culture are labelled with a DNA dye and separated based on the amount of DNA into a single cell cycle phase.

15. An assay as in claim 14, wherein the cell cycle phase is G1.

16. An assay as in claim 14, wherein the cell cycle phase is G2.

17. An assay as in claim 12, wherein the amount of fluorescence is measured in a fluorescence activated cell sorter.

18. An assay as in claim 12, wherein the amount of fluorescence is measured in a fluorescence analyzer.

* * * * *